United States Patent
McAteer et al.

(10) Patent No.: US 8,721,322 B2
(45) Date of Patent: May 13, 2014

(54) INJECTION MOLDING DEVICE AND METHOD

(75) Inventors: Vincent G McAteer, Jacksonville, FL (US); George B. Kipe, Yorba Linda, CA (US); Victor Lust, Jacksonville, FL (US); Phillip King Parnell, Sr., Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 244 days.

(21) Appl. No.: 13/307,569

(22) Filed: Nov. 30, 2011

(65) Prior Publication Data

US 2013/0134633 A1    May 30, 2013

(51) Int. Cl.
*B29C 45/02*    (2006.01)

(52) U.S. Cl.
USPC .................................... 425/543; 264/328.2

(58) Field of Classification Search
CPC ............... A61K 9/0051; B29C 2045/0094; B29C 45/02; B29K 2083/005; B29L 2031/753; B29L 2031/756
USPC ............ 264/250, 259, 328.1, 328.2; 425/542, 425/543
See application file for complete search history.

(56) References Cited

U.S. PATENT DOCUMENTS

| | | | |
|---|---|---|---|
| 3,949,750 A | 4/1976 | Freeman | |
| 4,426,341 A | 1/1984 | Tsuzuku et al. | |
| 5,053,030 A | 10/1991 | Herrick et al. | |
| 5,171,270 A | 12/1992 | Herrick | |
| 5,229,144 A | 7/1993 | Kuntz | |
| 5,283,063 A | 2/1994 | Freeman | |
| 5,417,651 A | 5/1995 | Guena et al. | |
| 5,423,777 A | 6/1995 | Tajiri et al. | |
| 5,723,005 A | 3/1998 | Herrick | |
| 5,962,548 A | 10/1999 | Vanderlaan et al. | |
| 6,020,445 A | 2/2000 | Vanderlaan et al. | |
| 6,099,852 A | 8/2000 | Jen | |
| 6,196,993 B1 | 3/2001 | Cohan | |
| 6,367,929 B1 | 4/2002 | Malden et al. | |
| 6,822,016 B2 | 11/2004 | McCabe et al. | |
| 8,282,386 B2 * | 10/2012 | Babin et al. | ................... 425/543 |
| 2011/0118685 A1 | 5/2011 | Nielsen et al. | |

FOREIGN PATENT DOCUMENTS

| | | |
|---|---|---|
| EP | 0995572 A1 | 10/1999 |
| EP | 1767331 A1 | 3/2007 |

OTHER PUBLICATIONS

European Search Report dated Jul. 18, 2013 for corresponding Application No. EP12194900.
"LSR" Micro-Shot, Internet Citation, Jun. 12, 2004, XP002410880; //web.archive.org/web/20040612000334/http://lawtomedical.com/lsr_microshot.html.
Partial European Search Report dated Mar. 12, 2013 for corresponding Application No. EP12194900.

* cited by examiner

*Primary Examiner* — Jill Heitbrink
(74) *Attorney, Agent, or Firm* — Carl J. Evens

(57) ABSTRACT

A micro silicone mold mounted plunger injection system comprises a silicone cartridge assembly, a micro plunger injection assembly and a cold deck nozzle assembly. In this system, these three components are interconnected directly such that it has a greatly reduced material flow path length and diameter. The system is capable of displacing an amount of material in a single shot substantially equal to the desired shot weight required to make a component.

7 Claims, 4 Drawing Sheets

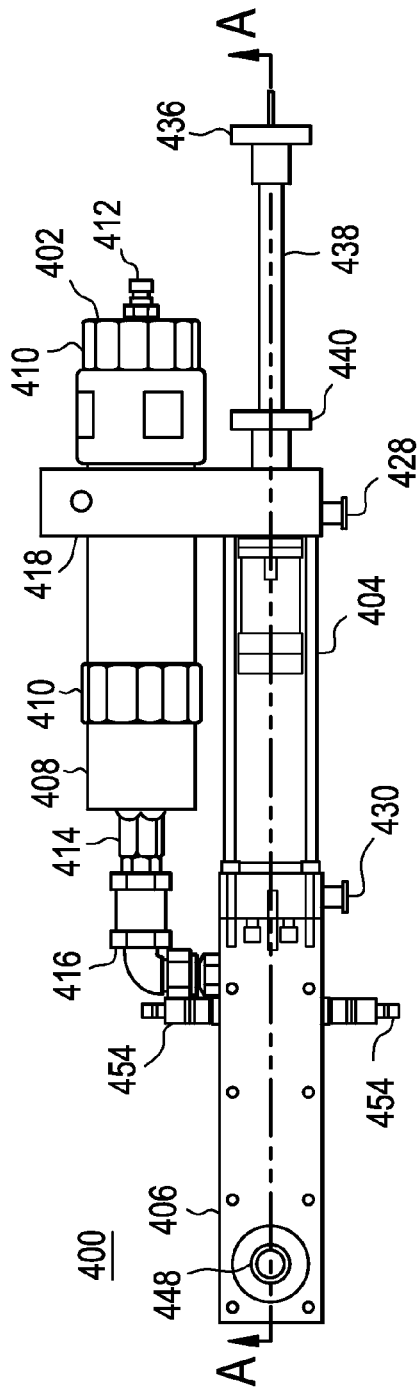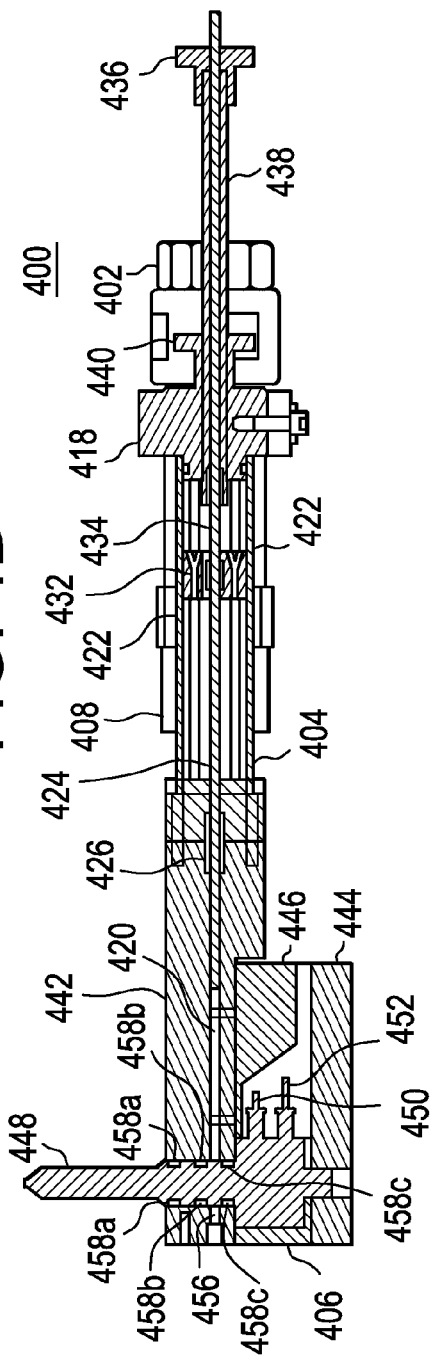

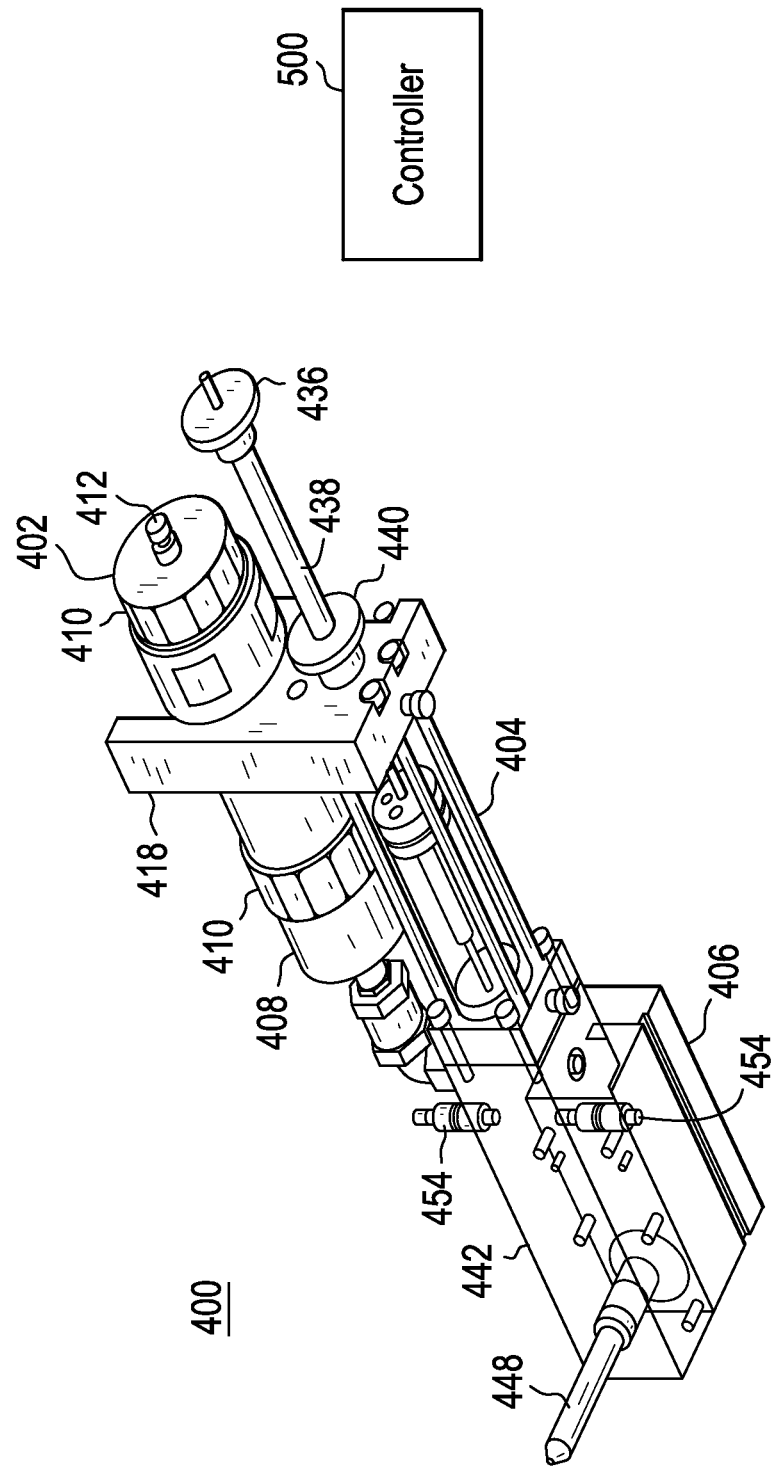

INJECTION MOLDING DEVICE AND METHOD

BACKGROUND OF THE INVENTION

1. Field of the Invention

The present invention relates to devices and methods for manufacturing medical devices, and more particularly to a fully automatic, miniature sized silicone molding cell that utilizes a novel silicone mold and plunger injection unit to produce a drug delivery device or portions thereof for use in the eye.

2. Discussion of the Related Art

The corner of each eye is called a canthus, with the nose side called the nasal canthus and the ear or temporal side called the temporal canthus. At the lower and upper eyelid margins of the nasal canthus are small openings called puncti or puncta. As used herein, both puncti and puncta shall be understood to be the plural form of punctum. Each punctum drains tears from the eyes. A punctal plug or occluder is an ophthalmic device for insertion into a punctum of an eye in order to treat one or more disease states. Typically, a punctal plug is positioned to block tear drainage thereby helping treat dry eyes. Punctal plugs may also be utilized for sustained release of medication to the eye for the treatment of a wide variety of ocular diseases.

In order to treat infection, inflammation, glaucoma, and other ocular diseases, drugs are often required to be administered to the eye. A conventional method of drug delivery is by topical application to the eye's surface. The eye is uniquely suited to this surface route of drug administration because, properly constituted, drugs can penetrate through the cornea, rise to therapeutic concentration levels inside the eye, and exert their beneficial effects. In practice, eye drops currently account for more than ninety-five (95) percent of drug delivery methods for the eye. Rarely are drugs for the eye administered orally or by injection, either because they reach the eye in too low a concentration to have the desired pharmacological effect, or because their use is complicated by significant systemic side effects.

Eye drops, though effective, are unrefined and inefficient. When an eye drop is instilled in the eye, it typically overfills the conjuctival sac, the pocket between the eye and the eyelids, causing a substantial portion of the drop to be lost due to overflow of the eyelid margin onto the cheek. In addition, a substantial portion of the drop remaining on the ocular surface is washed away by tears into the tear drainage system, thereby diluting the concentration of the drug. Not only is this share of the drug dose lost before it can cross the cornea, but this excess drug may be carried into the nose and throat where it is absorbed into the general circulation, sometimes leading to serious systemic side effects. The small portion of the drug in the eye drop which does penetrate the cornea results in an initial peak tissue concentration, a higher level than is required for the initial pharmacological effect. This tissue concentration then gradually decreases, such that by the time the next eye drop is due, the tissue concentration and the intended pharmacological effect may be too low.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Older patients may have additional problems instilling drops due to arthritis, unsteadiness, and decreased vision, and pediatric and psychiatric patient populations pose difficulties as well. Accordingly, punctal plugs provide a viable means for solving the problems of reliable and efficient drug delivery to the eye.

Punctal plugs may be of the temporary variety or of the permanent variety. Temporary punctal plugs are usually fabricated from collagen or other similar material and are dissolvable. Temporary punctal plugs may be utilized for short duration treatment or to gauge how an individual will react to having the insert placed, for example, will the device cause excessive tearing. Permanent punctal plugs are for long term use and are removable at any time. Permanent punctal plugs are available in various sizes with the largest size that fits providing maximum effectiveness. Permanent punctal plugs are typically made of silicone.

A punctal plug typically includes a body portion sized to pass through a lacrimal punctum and be positioned within a lacrimal canaliculus of the eyelid. The punctal plug also comprises a collarette connected to the body portion and sized to rest on the exterior of the lacrimal punctum. The term lacrimal punctum and lacrimal canaliculus are often utilized interchangeably; however, as used herein, the punctum means the opening and the canaliculus is the passageway or duct-like pathways that lead to the lacrimal sac. If the punctal plug is used to deliver therapeutic agents to the eye, then the body portion may comprise a reservoir for holding the therapeutic agents and the collarette may comprise an opening in communication with the reservoir through which the therapeutic agents are released.

Punctal plugs are small. For example, punctal plugs may be in the range of 0.2 to 0.4 millimeters in diameter and up to 2.0 millimeters in length. Devices so small are inherently more difficult to manufacture than larger devices. More importantly, manufacturing small devices in a repeatable and reliable manner is even more difficult. Accordingly, there exists a need for a micro mold and technology for producing or manufacturing punctal plugs with greater efficiency, even higher quality and higher repeatability than currently utilized technologies.

SUMMARY OF THE INVENTION

The injection molding device and method of the present invention overcomes the limitations associated with the prior art as briefly described above.

In accordance with one aspect, the present invention is directed to an injection molding device. The injection molding device comprising a cartridge assembly defining a chamber for housing a canister of premixed, one-to-one ratio mixture of thermoset elastomer, a cold deck nozzle assembly, the cartridge assembly being connected to the cold deck nozzle assembly through a one-way check valve and configured to inject thermoset elastomer from the canister into the cold deck nozzle assembly, the cold deck nozzle assembly comprising a manifold block with an internal passageway in fluid communication with the cartridge assembly and adapted to receive thermoset elastomer therefrom, and a cold deck nozzle in fluid communication with the internal passageway, and a micro plunger injection assembly connected directly to the cold deck nozzle assembly, the micro plunger injection assembly comprising a housing and a plunger moveable therein, the plunger configured to drive the thermoset elastomer through the internal passageway of the cold deck nozzle assembly and the cold deck nozzle, wherein the thermoset elastomer displacement for a single shot is substantially equal to the desired shot weight.

In accordance with another aspect, the present invention is directed to a method for injection molding a component. The method comprising moving a premixed, one-to-one ratio mixture of thermoset elastomer from a cartridge assembly securing a canister of the thermoset elastomer into an internal passage of a cold deck nozzle assembly, and driving the thermoset elastomer through the internal passageway of the cold deck nozzle assembly and a cold deck nozzle, wherein the thermoset elastomer displacement for a single shot is substantially equal to the desired shot weight of the component.

The micro silicone mold mounted plunger injection unit or system in accordance with the present invention is configured as a cold deck system. The micro silicone mold mounted plunger injection system comprises three main components; namely, a silicone cartridge assembly, a micro plunger injection assembly and a cold deck nozzle assembly all directly interconnected with one another, and controlled by a control system.

The micro silicone mold mounted plunger system of the present invention specifically reduces the flow path of silicone such that quality and reproducibility is increased while waste is reduced. In this system the injection unit is incorporated into the silicone mold extremely close to the cold shut-off nozzle. The system has a greatly reduced material flow channel diameter which is held constant up to the point of exiting the cold nozzle orifice. This provides a stable pressure constant within the system unlike that of a reciprocating screw system that begins with a larger diameter material channel and then reduces over the length of the flow path of the system. The actual injection stroke end position is located at the junction of the material flow channel and the cold shut-off nozzle. This arrangement and reduced material channel volumes significantly reduces material compression and pressure variation in the flow of the material thereby providing superior shot to shot repeatability.

The micro sized, direct mold mounted silicone plunger injection unit of the present invention offers a number of advantages, including the small size of the operating unit, a reduced material flow path volume, the elimination of pressure fluctuations in the material sub-system, a significant reduction in the variation in the injection process, a reduction in material waste and costs because of the single cartridge system, and the whole unit mounts directly onto the mold thereby eliminating a machine injection unit.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 4A is a diagrammatic representation of an exemplary micro silicone mold mounted plunger injection unit in accordance with the present invention.

FIG. 4B is a sectional view of the exemplary micro silicone mold mounted plunger injection unit illustrated in FIG. 4A taken along section line A-A.

FIG. 4C is a rotated view of the exemplary micro silicone mold mounted plunger injection unit illustrated in FIG. 4A.

DETAILED DESCRIPTION OF THE PREFERRED EMBODIMENTS

Figure 1:
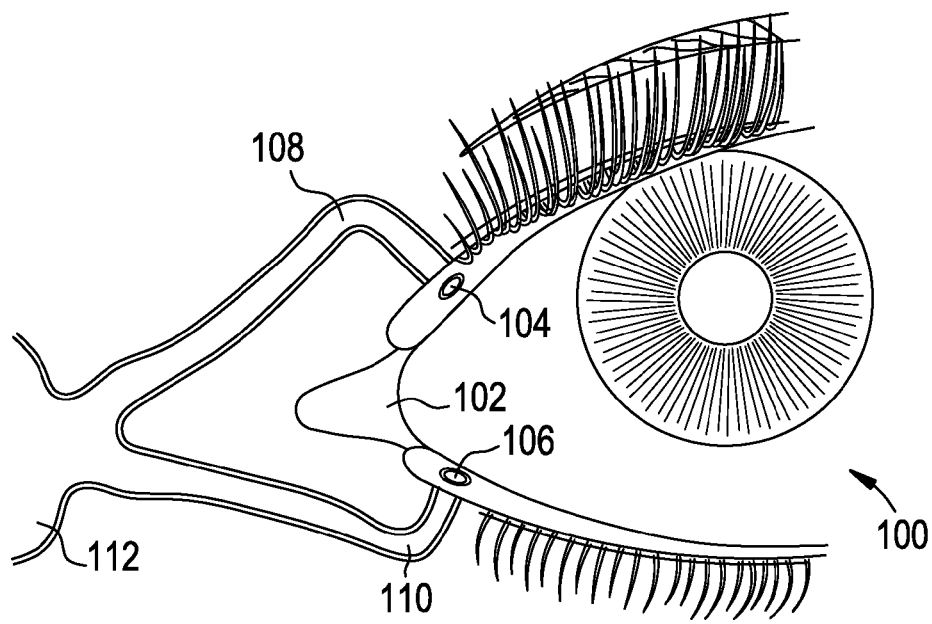
FIG. 1 illustrates the anatomy of the lacrimal drainage system of the human eye.

FIG. 1 illustrates the anatomy of the drainage system of a human eye 100. Tears are produced by the lacrimal gland, not illustrated, superior to the outer portion of each eye 100. Tears flow across the surface of the eye 100 to a shallow pool, termed the lacrimal lake 102, located where the upper and lower eyelids come together at their inner ends or nasal ends. From there, the tears drain through small openings in each of the eyelids, namely, the upper lacrimal punctum 104 and the lower lacrimal punctum 106. From the upper lacrimal punctum 104 and the lower lacrimal punctum 106, the tears pass into the upper lacrimal canaliculus 108 and lower lacrimal canaliculus 110, respectively, which are duct-like pathways leading to the lacrimal sac 112. The lacrimal sac 112 is the superior, expanded portion of the nasolacrimal duct, not illustrated, which drains tears into the nasal system. The upper lacrimal punctum 104 and associated canaliculus 108 typically only drain about ten percent of the tears from the eye 100, such that their obstruction virtually never leads to the tear overflow.

Tears or the tear film comprises three layers. The first layer or bottom layer is the layer that coats the eye and comprises mucin which is created by cells in the conjunctiva referred to as goblet cells. The mucin fills in microscopic irregularities on or in the eye's surface which is important to clear vision. The second layer or middle layer of the tear film comprises essentially water and makes up the bulk of the tear film. A majority of the watery component is produced or supplied from the main lacrimal or tear gland. Emotional tears and reflect tears, i.e. tears resulting from a stimulus such as bright light or a foreign body, come from the main lacrimal gland. Accessory lacrimal glands, known as the glands of Wolfing and Kraus are found in the eyelid tissue and also contribute to the watery component. The third or top layer of the tear film comprises a thin layer of oil secreted by the meibomian glands and functions to prevent the tears from evaporating too quickly.

Insufficient tears, or "dry eye" is a common condition caused by insufficient production of tears from the lacrimal gland which causes symptoms such as dryness, redness, burning, reflex tearing, itching, or foreign body sensation. In especially difficult cases of dry eye, a punctal occluder or punctal plug may be placed into one or both of the lacrimal puncta 104, 106, see FIG. 1. Punctal plugs prevent the tears, which are being produced in deficient volume by the lacrimal glad, from draining into the lacrimal canaliculi 108, 110. Punctal plugs may be secured in the lacrimal puncta without anesthesia and removed with ease when required.

Figure 2:
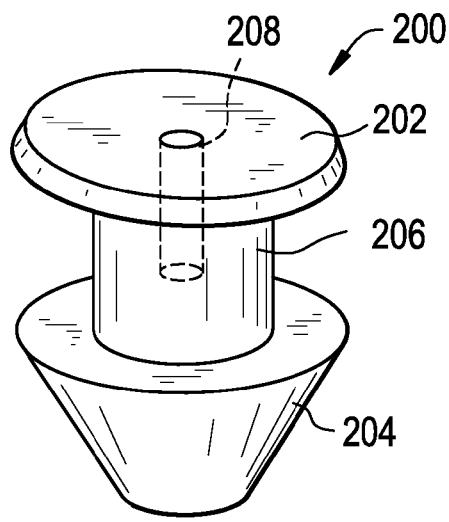
FIG. 2 illustrates an example of a conventional punctal plug that is known in the art.

Referring now to FIG. 2, there is illustrated an exemplary punctal plug 200. The punctal occluder or plug 200 comprises a collarette 202 which is configured to rest on the exterior of the punctum 104, 106 (FIG. 1), a bulb 204 that blockingly projects into the canaliculus 108, 110 (FIG. 1), and a body portion 206 connecting the collarette 202 and the bulb 204. Commercially available punctal plugs usually have a length of approximately 2.0 millimeters, and differ from each other only slightly in configuration. For example, the bulbs of the punctal plugs are designed to prevent the plug from being easily dislodged from the canaliculus, and may be tapered for ease of insertion into the puncta. The collerette is designed to have a diameter sufficient to prevent the plug from completely entering the canaliculus, and are preferably smooth to minimize irritation of the eye. The body portions of different punctal plugs are also similar in design and are essentially a non-functional connection between the collarette and the bulb portions. The collarette 202 may include an aperture 208, illustrated in phantom, extending into the body portion 206 to aid in grasping or securing the punctal plug 200 during its insertion into the puncta. Examples of punctal plugs may be found in U.S. Pat. Nos. 3,949,750 and 5,283,063 to Freeman, U.S. Pat. Nos. 5,053,030, 5,171,270 and 5,723,005 to Herrick, U.S. Pat. No. 5,417,651 to Guena et al., and U.S. Pat. No. 5,423,777 to Tajiri et al.

Figure 3:
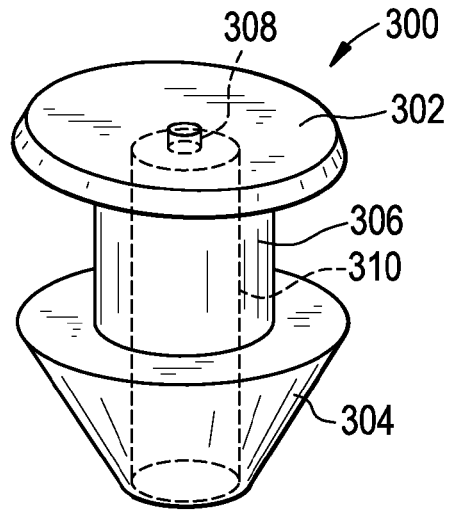
FIG. 3 illustrates an example of a punctal plug, including a reservoir for the release of one or more therapeutic agents, that is known in the art.

In addition to, or alternately, a punctal occluder or plug may be utilized to deliver one or more therapeutic agents and/or medications. FIG. 3 illustrates an ophthalmic insert or punctal plug 300 that adapts the form of a conventional punctal plug 200, as illustrated in FIG. 2, to incorporate a reservoir 310, illustrated in phantom, designed to store and release medication onto the surface of the eye. The reservoir 310 may be configured to release the medication in any number of ways, including pulsatile and continuous. In addition, the reservoir may be refilled as required. As in the previously described exemplary embodiment, the ophthalmic insert or punctal plug 300 comprises a collarette 302, a bulb 304 and a body portion 306. The punctal plug 300 may be molded or otherwise formed from a flexible material, such as silicone, that is impermeable to the medication which will fill the reservoir 310. Although silicone is described herein, it is important to note that any suitable biocompatible material may be utilized. The reservoir 310 may be formed by a channel through the interior of the body portion 306 of the plug 300. In one exemplary embodiment, the body portion 306 may be flexible, or even accordion shape so as to provide the capability of lengthwise expansion as it is filled with medication. The collarette 302 anchors the plug 300 to the exterior of the lacrimal punctum 104 and 106 (see FIG. 1) and may be provided with an opening 308 which is in fluid communication with the reservoir 310. In order to control the delivery of a specific medication, the geometry of the opening 308 may be customized in a variety of ways. For example, the opening 308 may be designed for releasing the medication at a constant sustained release rate, a pulsatile release rate, an exponential release rate and/or any combination thereof. Through opening 308, medication is released from the reservoir 310 into the tears of the lacrimal lake where the medication mixes, as eye drops do, with the tears and penetrate the eye to have the intended pharmacological and therapeutic effect. Although not required, the punctal plug 300 may comprise an enlarged bulb 304 to help secure the plug 300 in position within the canaliculus and also to provide additional volume for the reservoir as illustrated. An example of this type of punctual plug may be found in U.S. Pat. No. 6,196,993 to Cohan et al.

Punctal plugs may take on any number of configurations, sizes and be formed from any number of materials, depending on the desired functionality and/or medications to be delivered.

As set forth above, punctal plugs may take any size and shape. Typically, the body of the punctal plug is in the shape of an elongated cylinder, and may vary in length in the range from about 0.8 mm to about 5 mm and may vary in width in the range from about 0.2 mm to about 3 mm. The size of the opening for medication or drug release may be in the range from about 1 nm to about 2.5 mm. Rather than one large opening at any one location, multiple small openings may be used. The body of the punctal plug may be wholly or partially transparent or opaque. Optionally, the body may include a tint or pigment that makes the plug easier to see when it is placed in a punctum.

Punctal plugs may be fabricated from any number of suitable biocompatible materials including silicone, silicone blends, silicone co-polymers, for example, hydrophilic monomers of polyhdroxyethlmethacrylate, polyethylene glycol, polyvinylpyrrolidone and glycerol, and silicone hydrogel polymers, for example, those described in U.S. Pat. Nos. 5,962,548, 6,020,445, 6,099,852, 6,367,929, and 6,822,016. Other suitable biocompatible materials include polyurethane, polymethylmethacrylate, poly(ethylene glycol), poly(ethylene oxide), poly(propylene glycol), poly(vinyl alcohol), poly (hydroxyethylmethacrylate), poly(vinylpyrrolidone), polyarcrylic, poly(ethyloxazoline), poly(dimethyl acrylamide), phospholipids, for example, phosphoryl choline derivatives, polysulfobetains, acrylic esters, polysaccharides and carbohydrates, for example, hyaluronic acid, dextran, hydroxyethyl cellulose, hydroxyl propyl cellulose, gellan gum, guar gum, heparin sulfate, chondroitin sulfate, heparin and alginate, proteins, for example, gelatin, collagen, albumin and ovalbunin, polyamino acids, fluorinated polymers, for example, polytetrafluoroethylene and polyvinylidine fluoride, polypropylene, polyethylene, nylon and ethylene-co-vinylacetate.

The exterior surfaces of the punctal plug may be wholly or partially coated with a number of different biocompatible coatings. The coating may provide a number of benefits, including lubriciousness to aid in insertion of the device, muco-adhesiveness to improve tissue compatibility, texture to aid in anchoring the device and/or any combination thereof. Suitable biocompatible coatings include gelatin, collagen, hydroxyethyl methacrylate, poly(vinylpyrrolidone), poly (ethylene glycol), heparin, chondroitin sulfate, hyaluronic acid, synthetic and natural proteins, polysaccharides, thiomens, thiolated derivates of polyacrylic acid and chitosan, polyacrylic acid, carboxymethal cellulose and combinations thereof.

It has been found that with certain therapeutic agents or medications, it may be desirable to create a barrier layer between the therapeutic agent containing material to be released from the reservoir within the punctal plug and the interior surface of the walls that define the reservoir due to possible interactions, or inadvertent leaching of the active therapeutic agent through the wall of the punctal plug. In addition, it has been found that the retention of therapeutic agent within the reservoir may be aided by the selection of the geometric configuration of the punctal plug, or with the addition of various anchoring features. For example, a reservoir may comprise a simple cylindrical configuration which may not securely hold a particular therapeutic agent within the reservoir. In other words, that shape, even with a primer layer or adhesive layer may not be sufficient to hold the agent in place. Accordingly, the geometry of the reservoir may be modified to include protrusions or indents for holding the agent. These geometric variations may be utilized alone or in combination with various barrier layers, adhesives and/or primer layers. In other words, various combinations of geometries and coatings may be utilized to hold the drug in and/or force the drug out as required. For example, a barrier layer may be disposed on the external surface of the punctal plug to inhibit diffusion of the therapeutic agent in the body of the punctal plug and to inhibit the infusion of tears into the reservoir containing the therapeutic agent. In addition, the geometry of the punctal plug may be modified to create a better fit within the canaliculus.

Processes for manufacturing the punctal plugs are known in the art. Typically, the punctal plugs are manufactured by injection molding, cast molding, transfer molding, stamping, embossing or the like. Preferably, the reservoir is filled with one or more active agents, with or without other materials, subsequent to the manufacture of the device. The amount of active agent as well as other constituents, such as excipients, will depend on a number of factors, including the active agent or agents selected the desired release rate, and the melting points of the therapeutic agent. Preferably, the amount utilized is a therapeutically effective amount meaning an amount effective to achieve the desired treatment, inhibiting or prevention effect.

The present invention is directed to an automatic, miniature sized silicone molding cell that utilizes a novel silicone mold and plunger injection unit to produce a drug delivery device; namely, a punctal occluder or plug with a reservoir. In addition to producing punctual plugs, the injection unit may be utilized to produce components of punctual plugs as well as any extremely small device to be fabricated from a thermoset elastomer such as silicone.

Silicone molding in the medical, electronics, packaging and automotive industries is increasing due to a number of factors, including its hardness range (5 to 90 durometer), the fact that it is inert, odorless, tasteless, hypo-allergenic, it is flexible and durable and can be compounded for special properties. However, the injection molding of silicone rubbers is different than that of traditional thermoplastic injection molding. To mold a component with a thermoplastic requires that a thermoplastic resin be heated and injected into a cold mold. To mold a component with a silicone rubber requires that the liquid silicone rubber be kept cool and then injected into a heated mold. The design and manufacture of a silicone mold is also different from that of thermoplastic. The cold deck or the cold mold deck, as described in more detail subsequently, allows for the equal distribution of the silicone rubber to each cavity at the same hydraulic pressure and consistent temperatures profile.

The injection molding of silicone or liquid silicone rubber is a process utilized to manufacture or produce pliable, durable components in high volume. Silicone or liquid silicone rubber is a high purity platinum cured silicone having a low compression set, excellent stability and ability to resist extreme temperatures, both hot and cold. It is ideally suited for the production of components or devices where high quality is important, for example, in medical devices. Due to the thermosetting nature of the silicone, liquid silicone injection molding requires special treatment, including intensive distributive mixing while ensuring that the silicone remains at a low temperature prior to it being injected into a heated cavity or mold and vulcanized.

Chemically, silicone rubber is part of a family of thermoset elastomers that include a backbone of alternating silicon and oxygen atoms and methyl or vinyl side groups. Silicone rubber comprises about thirty (30) percent of the silicone family.

The typical liquid silicone injection molding machine or system comprises a number of functional components, including injectors, metering units, supply drums, mixers, nozzles, at least one mold clamp and mold. The injectors or injection device is responsible for pressuring the liquid silicone to facilitate injection of the silicone into the cavities of the mold. Pressure and injection rate may be adjusted automatically and/or manually to achieve various desired results. The metering units pump the two primary liquid materials; namely, the base forming silicone and the catalyst, ensuring that the two materials maintain a predetermined constant ratio while being simultaneously released. Supply drums serve as the primary containers for the unmixed materials. The supply drums as well as other containers, for example, containers holding pigmentation materials, are connected to the main pumping section of the system. A static and/or dynamic mixer combines the materials after they exit the metering units. Static mixing is typically utilized with simple mixing ratios and similar viscosities between the components to be mixed, whereas dynamic mixing is typically utilized with extreme mixing ratios and large differences between the viscosities of the components to be mixed. Once combined, pressure is used to drive the mixture into an injection unit, through an attached nozzle, and into a designated mold. Typically, the nozzle includes an automatic and/or manual shut-off value to prevent leakage and overfilling the mold. The mold clamp secures the mold during the injection molding process and is used to open the mold once the process is complete.

As briefly described above, the silicone molding of a part or component requires that the liquid silicone rubber be kept cool (60 to 77 degrees Fahrenheit) prior to being injected into a heated mold (340 to 410 degrees Fahrenheit). A runnerless molding system or cold deck is a device which allows for the equal distribution of material to each cavity at the same hydraulic pressure and consistent temperature profile. The raw materials utilized in the process are mixed in a one-to-one ratio, typically via the static mixer. Once the components come into contact, the curing process immediately begins. Accordingly, the cold drive is utilized to retard the curing process prior to the material being introduced into the heated mold. Essentially, the one-to-one mixed compound is pumped through the cold deck and then into a heated cavity where the vulcanization takes place. The cold deck and general cooling results in minimal loss of material as the injection occurs directly into the part, cavity or mold. This cooling process allows for the production of liquid silicone rubber parts with substantially zero material valve gate waste.

Silicone injection molding of micro sized components, such as punctal plugs or components of punctual plugs, in a conventional silicone injection molding machine is difficult due to the imbalance between the amounts of material flow relative to component volume. In other words, the high volume of material within the material flow path in conventional molding equipment is much greater than the volume of the micro sized components thereby eliminating the control system's ability to discern between filled and non-filled cavities.

The present invention is directed to a micro sized, plunger style, silicone injection unit that mounts directly into or onto a silicone mold along with a cold deck nozzle. The exemplary injection unit comprises a single material cartridge that feeds pre-mixed silicone directly through a one-way check valve into the plunger unit and the cold shut off nozzle of the cold deck mold. Pressure sensors/transducers mounted within the material flow path, as described in detail subsequently, and hard wired into the unit's control system monitor and control the injection sequencing and flow of the material through the injection unit. The plunger unit may comprise an electric motor, a pneumatically driven device or any other suitable means that is actuated by signals from the injection unit's control system based upon feedback signals from the sensors/transducers. The plunger unit works in conjunction with the cold nozzle shut off value to regulate mold cavity filling by pressure sensing rather than screw position or time like that in a conventional injection machine/process. Accordingly, the present invention eliminates the need for peripheral material pumping stations, lengthy material feed lines, and a conventional machine injection unit.

Essentially, the injection unit of the present invention simplifies the molding process associated with the micro silicone molding of punctal plugs, punctual plug components and/or any other micro sized devices. Although the exemplary injection unit described herein utilizes silicone, it is important to note that the present invention may be utilized with any suitable material for punctal plugs that can be injection molded and has molding properties similar to that of silicone and/or other thermoset elastomers for the reasons set forth above. Important to the performance of such a unit is shot to shot repeatability without compromising the mechanical and performance attributes of the punctal plug. The design and construction of the mold tool is critical in enhancing and optimizing part consistency and geometry. The present invention provides a simple and eloquent processing solution not based solely on tool and equipment miniaturization, but on reducing complexity, degrees of freedom and process variation.

Conventional technology uses high volume cavity tooling i.e. high volume as in a high number of cavities to fill, to compensate for volume control from cycle to cycle. This is done to overcome the large volume of a metered amount of material coming from the plasticizer/reciprocating module needed to generate some level of control with material volume and position accuracy. This becomes very difficult to control with very small shot sizes when one wants to control displacement and shot accuracy (variation increases with mold variations as explained by the power law). The current technology process flow may be briefly described as follows: In a first step, a silicone cross linker and plasticizer are statically and/or dynamically mixed in a mixing station. In a second step, the mixture is pumped into a metering/reciprocating plasticizer through an elaborate network of hoses from the mixing station. In a third step, the material is metered and dose determination is made by position and screw rotation. In a fourth step, the metered material is injected into a manifold for separation. In a fifth step, the material in the manifold is divided into equal amounts and deposited into the cold mold deck. The cold mold deck allows for the equal distribution of material to each cavity at the same hydraulic pressure and consistent temperature profile. In a sixth step, the material in the cold deck is injected into the mold cavity.

A much more simplified version of the injection unit or system in accordance with the present invention comprises a plunger unit which is attached directly into the cold deck, thereby substantially shortening the material flow path. The position and shot size may be accurately controlled utilizing a fine pitch position screw or a dc positional servo drive. The mold cavity is also directly mounted to the nozzle of the cold deck. The process flow in accordance with the present invention may be briefly described as follows: In a first step, a mixture, typically 1 to 1, of the silicone is loaded into 0.5 or half liter cartridges. In a second step, the 0.5 liter cartridge is attached directly to the plunger unit. With this direct attachment arrangement, there is no air contamination from hoses while establishing a shorter flow path. In a third step, the silicone is accurately positioned/metered into the cold deck drop. In a final step, the silicone is injected into the mold cavity. A more detailed description of the process is given subsequently.

The system of the present invention allows for very small shot sizes and more precision over the process with reduced variation as compared to the conventional system described above. Direct plunging into the cold deck provides for more control over material compressibility, pressure, part geometry and temperature during the high pressure fill and cure cycle and very accurate shot design technology. The control logic sequence of the plunger provides for silicone from the cartridge to be delivered by regulator controlled air pressure into the plunger unit through a one-way check valve, then when signaled, the plunger and nozzle valve open simultaneously and the plunger rod drives the pre-set dose of silicone through the feed channel into the mold, and the nozzle valve closes and the plunger retracts to its shot recharge position. This is accomplished by regulator controlled air pressure to about 0.8 bar. The plunger unit comprises a 3 mm diameter plunger with fine stroke position by screw and digital micrometer or linear encoder. This plunger unit is a stand-alone unit that is easy to repair and overhaul. It is important to note that while the device as described and illustrated is pneumatic in terms of piston control as well as a number of other features, any suitable alternate means may be utilized.

Referring to FIGS. 4A, 4B and 4C, there is illustrated an exemplary micro silicone mold mounted plunger injection unit or system 400 in accordance with the present invention. FIG. 4B is a cross-sectional view of the system 400 illustrated in FIG. 4A taken along section line A-A and FIG. 4C is a rotated view of the system 400 illustrated in FIG. 4A. The entire system 400 is configured as a cold deck system and comprises three main components; namely, a silicone cartridge assembly 402, a micro plunger injection assembly 404 and a cold deck nozzle assembly 406.

The silicone cartridge assembly 402 comprises a cylindrical canister 408 with at least one threaded connector 410 and a pneumatic connection port 412. The silicone cartridge assembly 402 is connected to the cold deck nozzle assembly 406 via a simple piping arrangement 414 which includes a check valve 416. The check valve 416 prevents back pressure from the compressed material in the system, described in more detail below, from forcing silicone back into the silicone cartridge assembly 402. The silicone cartridge assembly 402 is secured to the micro plunger injection assembly 404 via bracket 418. A container, not illustrated, comprising a pre-mixed, one-to-one (1:1) silicone mixture is positioned in the cylindrical canister 408 such that pneumatic pressure from port 412 forces the silicone mixture through the check valve 416 and into an internal passage 420 of the micro plunger injection assembly 404/cold deck nozzle assembly 406 in a controlled manner. A control system, 500, controls and coordinates the timing of silicone movement through the system 400 as is described in detail subsequently. Although pneumatic pressure is utilized to force or drive silicone from the silicone cartridge assembly 402, any other suitable means may be utilized.

The micro plunger injection assembly 404 comprises a housing 422 through which a plunger rod 424 travels. This plunger rod 424 is utilized to force the silicone through the internal passage 420 of the cold deck nozzle assembly 406 based on commands by the control system 500. The plunger rod 424 may vary in size from 0.5 mm to 6.5 mm and the internal passage or bore 420 is sized accordingly. A plunger seal pack 426 seals the plunger rod 424 at the various sizes (0.5 mm to 6.5 mm). The housing 422 surrounds and secures the plunger rod 424 therein. The plunger rod 424 may be driven pneumatically, via an electric servo motor or any other suitable means. In the illustrated exemplary embodiment, the plunger rod 424 is driven pneumatically via two pneumatic ports 428 and 430. When port 428 is pressurized via commands from the control system 500, the plunger rod 424 moves forward driving the silicone through the cold deck nozzle assembly 406 and into a mold cavity, not illustrated. This injection is timed with the operation of the cold nozzle assembly 406. When port 430 is pressurized via commands from the control system 500, the plunger rod 424 moves backward and silicone enters the material channel and is moved through the cold deck nozzle assembly 406 and the system 400 is recharged and ready to execute the next injection or shot of silicone to form a part. A plunger rod piston O-ring 432 is positioned around the plunger rod 424 proximate a plunger rod indicator flag 434. A shot adjusting knob 436 connected to a shot adjuster 438 may be utilized to set or fine tune the size of the silicone shot to be injected into the cavity mold. In other words, the shot adjuster 438 may be utilized to set the number of micrograms of silicone to be ejected from the cold deck nozzle assembly 406 in a single shot. The shot adjuster 438 passes through a threaded lock nut 440 mounted to the housing 422 such that by simply turning the knob, 436 more or less silicone may be ejected based on the throw of the plunger rod 424. As set forth above, the plunger rod 424 in this exemplary embodiment is 3 mm in diameter and the injection stroke length is adjustable via the shot adjuster 438 and lock nut 440, both of which include fine threads for precise adjustment. A manifold block 442 with inside bore or internal passage 420, in which the silicone flows to the cold nozzle 448, is mounted to the end of the micro plunger injection assembly 404 opposite that of the shot adjuster 438 end.

The cold deck nozzle assembly 406 is directly connected to both the silicone cartridge assembly 402 and the micro plunger injection assembly 404. The cold deck nozzle assembly 406 comprises a nozzle holding base 444, a cold nozzle holding block 446 and the cold nozzle 448. The cold nozzle 448 comprises two pneumatic inlet ports 450 and 452 which control an internal valve, described in detail subsequently, that opens and closes the cold nozzle 448. Control signals from the controller 500 open the nozzle 448 for delivery of a shot and close the nozzle 448 after the shot has been delivered or between shots. As before, any other suitable means may be utilized to open and/or close the nozzle 448. The cold deck nozzle assembly 406 also comprises water circulating ports 454 which provide chilled water to the cold deck nozzle assembly 406 in order to maintain the temperature of the silicone at the optimum working temperature. The water is utilized to maintain the silicone at a temperature range of about seventeen (17) to about twenty (20) degrees Celsius. A pressure sensor/transducer 456 is mounted in line with internal passage 420 on the opposite side of the cold nozzle 448. As set forth above, the pressure sensor/transducer 456 is hard wired into the control system 500 to control the injection sequencing and flow of material through the system 400. O-ring seals 458a, 458b and 458c are positioned around the cold nozzle 448 to prevent water from contacting the silicone.

Figure 5:
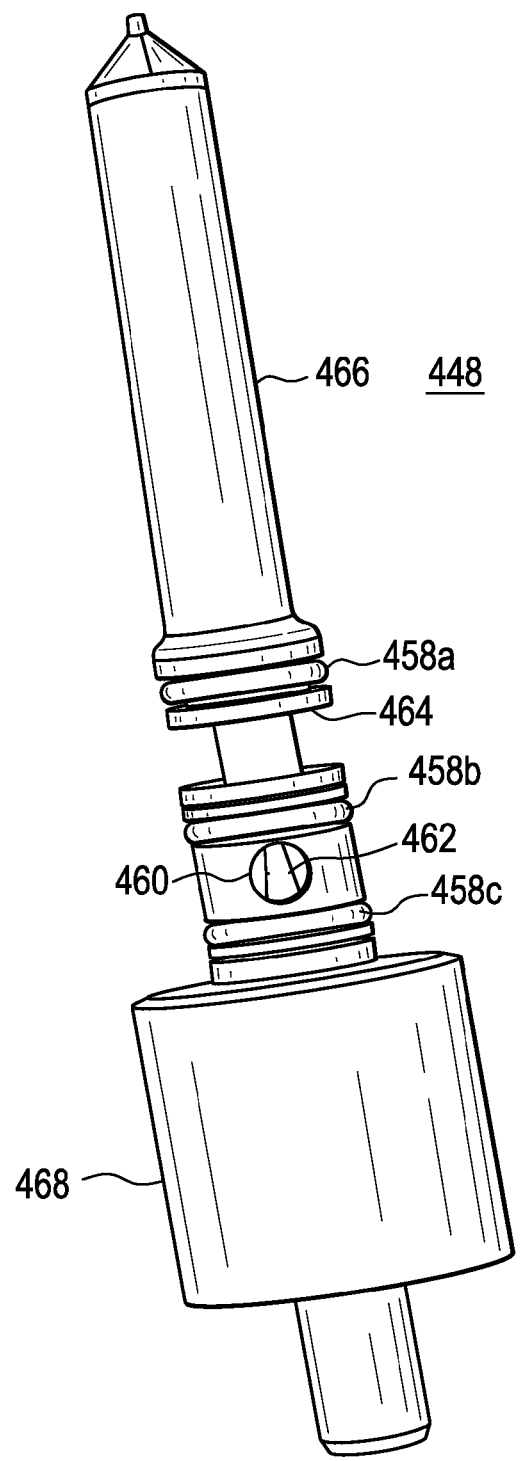
FIG. 5 is a diagrammatic representation of a cold deck nozzle assembly in accordance with the present invention.

FIG. 5 illustrates a detailed and expanded view of the cold nozzle 448. As illustrated, the O-ring seals 458a, 458b and 458c are positioned in grooves of the cold nozzle 448 to provide a sealed separation between the silicone material flow and cooling water flow channels. Silicone material enters the cold nozzle through orifice or opening 460 located between O-rings 458b and 458c and flows up around the shut-off valve or pin 462. Water enters the cold nozzle 448 through a channel 464 between O-rings 458a and 458b and flows up, around and then back down inside of the long slim portion 466 of the nozzle assembly 448. The large body section 468 of the assembly comprises the nozzle shut-off pin piston assembly that opens and closes the nozzle 448. As described above, pneumatic inlet ports 450 and 452 supply the air pressure to open and/or close the nozzle 448.

The exemplary micro silicone mold mounted plunger unit or system 400 functions as set forth in detail below. When molding parts or components, silicone from the silicone cartridge assembly 402 is driven into the micro plunger injection assembly 404 via controlled air pressure regulated by the control unit 500. Silicone in the inside bore or internal passage 420 is driven through the cold nozzle 448 of the cold deck nozzle assembly 406 via commands from the control system 500 and into the mold cavity. The control unit of system 500 is programmed to run the entire process in accordance with a preferred procedure. The control system 500 is a feedback based system that may be implemented in any suitable manner, including through the use of a micro-controller. The control unit of system 500 is programmed to run the entire process in accordance with a preferred procedure. The control system 500 is a feedback system that may be implemented in any suitable manner, including the use of a micro-controller. As set forth herein, the shot size is determined by the stroke of the plunger rod 424 which may be adjusted manually by the shot adjuster 438, or from the controller to a servo drive. Silicone flow itself from the cold nozzle 448 is controlled via the control system 500 through the cold nozzle valve.

Table 1 below summarizes the displacement for the system 400 of the present invention. As set forth, for a thirty (30) mm stroke, the silicone displacement is 0.0144 cubic inches or 0.211 grams for a single shot. For a comparison, Table 1 also summarizes the displacement for currently utilized 12 mm diameter reciprocating screw devices. For a thirty (30) mm stroke in the reciprocating system, the silicone displacement is 0.2069 cubic inches or 3.3905 grams. This is 14.3 times more silicone for a single shot. As may be readily understood, there is significant increase in compression of material associated with the reciprocating screw devices currently utilized which result in material flow variation. The reciprocating screw systems are independent from the silicone mold which adds material flow distance into the system. Here the silicone must flow from the material inlet port on the barrel and be augured along the screw until it is compressed ahead of the screw tip. From here the material must travel through the machine nozzle to enter the mold and then be distributed equally to each cavity. This entire system is subject to material compressibility which equates to variation in material pressure and flow rate.

The exemplary micro silicone mold mounted plunger unit or system 400 of the present invention specifically reduces the flow path of silicone such that quality and reproducibility is increased while waste is reduced. In this system the injection unit is incorporated into the silicone mold extremely close to the cold shut-off nozzle. The system has a greatly reduced material flow channel diameter which is held constant up to the point of exiting the cold nozzle orifice. This provides a stable pressure constant within the system unlike that of a reciprocating screw system that begins with a 12 mm diameter material channel and then reduces over the length of the flow path of the system. The actual injection stroke end position is located at the junction of the material flow channel and the cold shut-off nozzle. This arrangement and reduced material channel volumes significantly reduces material compression and pressure variation in the flow of the material thereby providing superior shot to shot repeatability.

As set forth in Table 1, the material displacement, 0.211 grams, for a single shot is substantially equal to the desired total shot weight of 0.218 grams. This is only achievable with the design of the present invention given the direct connections and extremely short flow paths. With the micro plunger injection assembly connected directly to the cold deck nozzle assembly, the plunger rod drives the thermoset elastomer, silicone, through the internal passageway or bore of the cold deck nozzle assembly and the cold deck nozzle.

TABLE 1

| Injection Type | Out total shot weight is 0.218 gr | Rod/Screw "Area" (Cubic inches) | Material Displacement (cubic inches) | Material Displacement (Grams) |
|---|---|---|---|---|
| Plunger | Stroke maximum is 50 mm | 0.0129 | | |
| | Stroke minimum is 1 mm | 0.0129 | | |
| | Stroke used is 30 mm | 0.0129 | | |
| | The 3 mm diameter plunger has an area of | 0.0129 | | |
| | Displacement of 3 mm rod @ 30 mm stroke = | | 0.0144 | 0.211 |
| | Displacement of 3 mm rod @ 1 mm stroke = | | 0.0004 | 0.0066 |
| | Displacement of 3 mm rod @ 50 mm stroke = | | 0.0214 | 0.3516 |
| Reciprocating Screw | A 12 mm diameter reciprocating screw has an area of | 0.752 | | |
| | Displacement of 12 mm diameter screw @ 30 mm stroke = | | 0.2069 | 3.3905 |

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An injection molding device comprising:
   a cartridge assembly defining a chamber for housing a canister of premixed, one-to-one ratio mixture of thermoset elastomer, the chamber of the cartridge assembly comprises a substantially tubular member having a removable section for at least one of insertion or removal of the canister;
   a cold deck nozzle assembly, the cartridge assembly being connected to the cold deck nozzle assembly through a one-way check valve and configured to inject thermoset elastomer from the canister into the cold deck nozzle assembly, the cold deck nozzle assembly comprising a manifold block with an internal passageway in fluid communication with the cartridge assembly and adapted to receive thermoset elastomer therefrom, and a cold deck nozzle in fluid communication with the internal passageway, the cartridge assembly further comprises a mechanism for driving the thermoset elastomer into the cold deck nozzle assembly; and
   a micro plunger injection assembly connected directly to the cold deck nozzle assembly, the micro plunger injection assembly comprising a housing and a plunger moveable therein, the plunger configured to drive the thermoset elastomer through the internal passageway of the cold deck nozzle assembly and the cold deck nozzle, wherein the thermoset elastomer displacement for a single shot is substantially equal to the desired shot weight.

2. The injection molding device according to claim 1, wherein the cold deck nozzle assembly further comprises a nozzle holding base, a cold nozzle holding block, and a chilling mechanism, wherein the nozzle holding base and the cold nozzle holding block secure the cold deck nozzle in position and allow for fluid communication between the cold deck nozzle and the internal passageway of the manifold block.

3. The injection molding device according to claim 2, wherein the chilling mechanism comprises a series of passageways for circulating cooling water.

4. The injection molding device according to claim 3, wherein the micro plunger injection assembly further comprises a plunger seal pack operatively associated with the plunger and an arrangement for moving the plunger to drive the thermoset elastomer through the internal passageway of the cold deck nozzle assembly and the cold deck nozzle and to a recharge position.

5. The injection molding device according to claim 4, wherein the micro plunger injection unit further comprises a shot stroke adjustment mechanism for setting the stroke length for a given shot.

6. The injection molding device according to claim 5, wherein the cold deck nozzle comprises a valve to open and close the cold deck nozzle.

7. The injection molding device according to claim 1, wherein the device further comprise a control system for controlling the operation of at least one of the cartridge assembly, the cold deck nozzle assembly and the micro plunger injection assembly.

* * * * *